United States Patent [19]

Peterson

[11] 4,137,240

[45] Jan. 30, 1979

[54] HYDROFORMYLATION PROCESS FOR PREPARATION OF PREDOMINANTLY LINEAR ALDEHYDES

[75] Inventor: Marvin L. Peterson, Woodstown, N.J.

[73] Assignee: E. I. Du Pont de Nemours and Company, Wilmington, Del.

[21] Appl. No.: 809,188

[22] Filed: Jun. 23, 1977

Related U.S. Application Data

[63] Continuation-in-part of Ser. No. 753,455, Jan. 31, 1976, abandoned.

[51] Int. Cl.$^2$ ............................................. C07D 319/04
[52] U.S. Cl. .......................... 260/340.7; 260/340.9 R; 260/599; 260/604 HF; 560/262
[58] Field of Search ...................... 260/340.7, 340.9 R

[56] References Cited

U.S. PATENT DOCUMENTS

| | | | |
|---|---|---|---|
| 3,527,809 | 9/1970 | Pruett et al. | 260/604 |
| 3,929,915 | 12/1975 | Cumbo et al. | 260/340.7 X |
| 3,963,754 | 6/1976 | Cumbo et al. | 260/340.7 X |
| 4,003,918 | 1/1977 | Hughes | 260/340.7 |

OTHER PUBLICATIONS

Marko et al., Magyar Asvanyolajes Foldgazkiserleti Integet and Peti Nitrogenmuvek, Hung. 152,607 (Cl. C07C), Jan. 22, 1966.

Pino et al., Chem. Ind. (Milan), 50(1), 106–118 (1968) (Ital.).

Primary Examiner—Ethel G. Love

[57] ABSTRACT

A process for the hydroformylation of terminally unsaturated olefinic compounds by carrying out the hydroformylation under a continuously decreasing partial pressure of carbon monoxide to achieve a high linear to branched-chain ratio of aldehydes without a reduction in reaction rate, said process comprising conducting the hydroformylation at an initial total carbon monoxide and hydrogen pressure of from 40 to 500 psia the mole ratio of hydrogen to carbon monoxide being 1:1 or greater and adjusting downward the partial pressure of CO continuously until at least a 25% reduction in the partial pressure of carbon monoxide in the range of from 1 to 40 psi absolute is reached.

11 Claims, No Drawings

HYDROFORMYLATION PROCESS FOR PREPARATION OF PREDOMINANTLY LINEAR ALDEHYDES

CROSS REFERENCE TO RELATED APPLICATION

This is a continuation-in-part of copending application Ser. No. 753,455, filed Jan. 31, 1977, now abandoned.

BACKGROUND OF THE INVENTION

1. Field of Use

This invention relates to an improved process for the preparation of aldehydes having a high ratio of linear aldehydes to branched-chain aldehydes from terminally unsaturated olefins by adjusting the carbon monoxide partial pressure downward during the hydroformylation of said olefins. More specifically, this invention relates to a process for preparing aldehydes having a high ratio of linear to branched chains by substantially continuously reducing the carbon monoxide partial pressure in the hydroformylation of terminally unsaturated olefins.

2. Prior Art

Processes, known as the oxo process and also as hydroformylation, involving the preparation of reaction mixtures containing substantial amounts of aldehydes by the catalytic reaction of olefinic compounds with carbon monoxide and hydrogen at elevated temperatures and pressures are known in the art. The aldehydes produced in said processes correspond to compounds obtained by addition of a carbonyl group and hydrogen to the olefinic bond. However, in such processes the ratio of straight-chain (linear) aldehydes to branched-chain aldehydes is relatively low.

U.S. Pat. No. 2,880,241 discloses that rhodium-containing catalysts are effective for the hydroformylation of olefins and that at low temperatures, such as 60° to 120° C., they permit the production of predominantly (75 to 90%) branched isomer.

U.S. Pat. No. 3,527,809 claims a process for production of oxygenated products comprising aldehydes having high ratios of normal to branched-chain isomers by hydroformylating an alpha olefinic hydrocarbon with carbon monoxide and hydrogen in the presence of a complex catalyst of rhodium with carbon monoxide and a triorgano phosphorous ligand and excess free ligand at temperatures of 50° to 145° C. and a partial pressure of carbon monoxide of from 25% to 75% or 90% of a total pressure of carbon monoxide and hydrogen of less than 450 psia. However, the reference clearly discloses continuous or stepwise addition of carbon monoxide and hydrogen during said hydroformylation to maintain the carbon monoxide and hydrogen pressure at a predetermined constant level.

SUMMARY OF THE INVENTION

Now it has been found that exceptionally high overall linear to branched-chain aldehyde isomer ratios can be produced by the hydroformylation of a terminally unsaturated olefinic compound in the presence of a complex catalyst of rhodium with carbon monoxide and a triorgano phosphorous ligand when the partial pressure of carbon monoxide is essentially continuously reduced as the reaction proceeds. Thus, it has been found that a reduction of the carbon monoxide partial pressure stepwise or continuously as the reaction proceeds prevents a decrease in the ratio of linear branched chain aldehyde and maintains a high production of linear isomer. By the process of the present invention the linear aldehyde can be selectively produced in high yields, which heretofore have not been possible without a reduction in reaction rate.

Accordingly, the process of the invention for preparing aldehydes having a high ratio of linear to branched chains comprises (a) initiating the hydroformylation of a terminally unsaturated olefinic compound in the presence of rhodium containing complex catalyst of a tertiary organo phosphorous ligand, under a total pressure of 40 to 500 psia, preferably 60 to 200 psia, of hydrogen and carbon monoxide wherein the mole ratio of hydrogen to carbon monoxide is at least 1:1 and that partial pressure of carbon monoxide is from 20 to 200 psia, preferably 30 to 60 psia;

(b) reducing stepwise or continuously the partial pressure of carbon monoxide as the reaction in (a) proceeds until at least a 25% reduction in carbon monoxide partial pressure is attained and the partial pressure of carbon monoxide is from 1 to 40 psia, preferably 5 to 20 psia; and the total pressure of hydrogen and carbon monoxide is from 20 to 300 psia, preferably 20 to 60 psia; and (c) separating the aldehydes thus prepared from the reaction product.

A novel feature of the process of the invention is the preparation of an aldehyde having an exceptionally high ratio of linear to branched-chain isomers by reducing the carbon monoxide partial pressure stepwise or continuously as the reaction of an olefinic compound with carbon monoxide and hydrogen in the presence of rhodium complex catalysts with an organo phosphorous ligand process.

It was found that in the catalytic hydroformylation of olefinic compounds, at constant hydrogen and carbon monoxide partial pressures, the linear/branched aldehyde isomer ratio declines continuously as the reaction progresses. Quite surprisingly it was discovered that the decreasing of the ratio of linear to branched-chain aldehydes that occurs in the hydroformylation of olefins over rhodium complex catalysts at constant hydrogen and carbon monoxide pressure can be stopped. The process of the present invention stops the decrease in linear aldehyde formation that occurs as the hydroformylation reaction progresses by adjusting downwardly the partial pressure of carbon monoxide.

Though we do not wish to be held to any theory that would explain the role of the carbon monoxide, we believe the amount of linear product in the present process is dependent on the carbon monoxide in solution. The active catalyst complex, also referred to herein as rhodium complex and complex rhodium catalyst, contains a concentration of triorgano phosphorous ligand and carbon monoxide equal to a total of four moles complexed with one mole of rhodium. Thus, the active species may comprise a mixture of complexed catalysts characterized by one, two or three triorgano phosphorous molecules with complimentary molecules of carbon monoxide to a total of four ligands. The ultimate composition of the complex catalyst may be the result of competing reactions between carbon monoxide and the triorgano phosphorous ligand for complexing sites with rhodium. These competing reactions can be influenced by changes (a) in the partial pressure of carbon monoxide or (b) in the concentration of triorgano phosphorous ligand. Active complex catalysts containing the maximum molecules (3) of triorgano phosphorous ligand and minimum molecules (1) of complex carbon monoxide are preferred species for producing the linear aldehyde product. A low concentration of carbon monoxide in solution provides conditions for maximum production of linear aldehyde product.

In the early stages of the hydroformylation when the olefin concentration is the greatest, even at low catalyst concentrations (about $10^{-4}$ moles Rh per mole of olefinic compound), the reaction is very fast provided the mixing of gas and liquid is sufficient to reduce gas to liquid mass transfer dependency. Also in the early stages of said reaction when the olefin concentration is the greatest, the carbon monoxide is reacted so rapidly that only minute concentrations thereof in solution are possible. The reaction product at this stage when the rhodium is complexed with the aforesaid maximum number of triorgano phosphosous ligands and the olefin concentration is greatest is largely linear aldehyde product. The relationship between gas to liquid mass transfer and carbon monoxide concentration and reaction products has heretofore not been recognized.

As the olefinic reactant becomes diluted with product aldehyde, the reaction rate is slowed, the rate of carbon monoxide use is reduced, the dynamic concentration of carbon monoxide in solution increases and the composition of the complex rhodium catalyst changes to include more carbon monoxide. As the complex catalyst includes more carbon monoxide and less triorgano phosphorous the reaction produces less linear aldehyde. Under the present process, the decrease in partial pressure of carbon monoxide maintains a low concentration of carbon monoxide in solution which causes the complex catalyst to contain less carbon monoxide and more triorgano phosphorous which favors the production of linear aldehyde. The relatively high pressure of carbon monoxide that may be present in the early stages of the present process results in an overall reaction rate that is more rapid.

The dynamics of the reaction as determined by the interacting variables of carbon monoxide partial pressure, rhodium concentration, ligand concentration and reaction temperature dictate the optimum carbon monoxide partial pressure at the start and close of the reaction.

In addition to the higher linear aldehyde production of the present invention, there is achieved a higher overall rate of reaction than when the carbon monoxide is not continuously reduced during the reaction.

Any terminally unsaturated olefinic compound which does not contain other functional groups that react with the catalyst or ligand or other components of the reaction mixture may be hydroformylated by the process of the invention. The terminally unsaturated olefinic compounds of the invention are limited to cyclic and acyclic olefins having 3 to 20 carbon atoms. The process of the invention is particularly well suited for hydroformylation of the cyclic acetals of acrolein, such as 2-vinyl-4-methyl-1,3-dioxane. Representative terminally unsaturated olefinic compounds include 2-vinyl-5-methyl-1,3-dioxane, 2-vinyl-1,3-dioxane, 2-vinyl-4,4,6-trimethyl-1,3-dioxane, 2-vinyl-4,5-dimethyl-1,3-dioxolane, propylene, 1-butene, 1-pentene, 1-hexane, 1-heptene, 1-octene, 1-octadecene, styrene, vinyl acetate, allyl acetate, vinyl propionate, allyl propionate, vinyl ethyl ether and allyl ethyl ether.

The hydroformylation type of complex catalysts of this invention are defined as coordination catalysts formed by the union of one or more electronically rich molecules or atoms capable of independent existence with one or more electronically poor molecules or atoms each of which are also capable of independent existence. These coordination catalysts, referred to herein also as complex catalysts, involve rhodium bonded to ligands by coordination bonds.

The rhodium complex catalyst of the present invention is a homogeneous catalyst solution comprising rhodium and biphyllic ligands complexed with carbon monoxide through coordinate bonding. The biphyllic ligands contain an atom selected from Group V-A of the Periodic Chart, preferably trivalent phosphorous or arsenic. The most preferred tertiary organo phosphorous compounds are compounds selected from the group consisting of trialkyl phosphites, triaryl phosphites, tiralkyl aryl phosphites, trialkyl phosphines and triaryl phosphines.

The triaryl phosphites and trialkyl phosphites are represented by the general formula

wherein $R_1$, $R_2$ and $R_3$ are the same or different alkyl or aryl groups having 1 to 12 carbon atoms. Representative examples of such alkyl groups include methyl, ethyl, propyl, octyl, pentyl, decyl and dodecyl. Representative examples of aryl groups include phenyl, tolyl, p-chlorophenyl, diphenyl and cyanophenyl. Representative examples of the phosphite ligand include trimethyl phosphite, triethyl phosphite, tri-n-propyl phosphite, triisopropyl phosphite, tri-n-butyl phosphite, triisooctyl phosphite, dimethyl dodecyl phosphite, tridecyl phosphite, methyl ethyl propyl phosphite, triphenyl phosphite, tri(p-chlorophenyl) phosphite, tri(cyanophenyl) phosphite, tri(p-methoxyphenyl) phosphite, tri(-diphenyl) phosphite, dimethyl phenyl phosphite, ethyl ditolyl phosphite and other combinations within the scope of the above formula.

The triaryl phosphine and trialkyl phosphine ligands of the invention are known in the art. The alkyl and aryl groups of the phosphine ligands are as defined above for the phosphite ligands. Representative examples of triaryl phosphines include triphenyl phosphine, tritolyl phosphine, dimethylphenyl phosphine, ethyl ditolyl phosphine, trinaphthyl phosphine and others within the above definition. Representative examples of trialkyl phosphines include trioctyl phosphine, tridodecyl phosphine, diethyl dodecyl phosphine and dimethyleicosyl phosphine.

The complex catalyst ligand may also be a triaryl arsine. Representative examples of such ligand include triphenyl arsine, tritolyl arsine and tri-p-chlorophenyl arsine.

The phosphite ligands are preferred. The phosphite ligands wherein $R_1$, $R_2$ and $R_3$ are methyl, ethyl, n-propyl, isopropyl and phenyl are more preferred. Triphenyl phosphite is the most preferred ligand.

The ligand forms a complex with rhodium and carbon monoxide as described in U.S. Pat. No. 3,527,809 and the complex catalyzes the hydroformylation reactions of the present invention. An excess of the ligand over that which is required to complex the rhodium must be used in order to insure the most desired 3:1 ratio of ligand to CO in the complex. The excess ligand is also necessary to insure the stability of the metal, e.g., rhodium catalyst throughout the hydroformylation reaction.

The combined hydrogen and carbon monoxide pressure at which the process of the present invention is initiated may range from 40 to 500 psia, preferably 60 to 200 psia. The process of this invention is generally operable at initial carbon monoxide partial pressures of from 20 to 200 psia. Preferably, the carbon monoxide partial pressure initially is in the range of from 30 to 60 psia. The partial pressure of carbon monoxide is decreased continuously or stepwise over the duration of they hydroformylation process of the present invention until at the end of the reaction the carbon monoxide partial pressure is from 1 to 40 psia, preferably 5 to 20 psia. In order to achieve a significant improvement in the linear to branched aldehyde ratio over constant pressure operations, the carbon monoxide partial pressure during the hydroformylation reaction is reduced at least 25%. The final total pressure of carbon monoxide and hydrogen is 20 to 300 psia and most preferably 20 to 60 psia. The reduction in carbon monoxide partial pressure generally is at least 25%. It is preferred to conduct the process of this invention to achieve at least a 50% reduction of carbon monoxide partial pressure; while a carbon monoxide partial pressure reduction of 50 to 75% is most preferred. At reductions of less than 25%, the improvement in the linear to branched aldehyde ratio over said ratio at constant pressure is less significant.

The mole ratio of hydrogen to carbon monoxide fed into the hydroformylation reaction initially is at least 1:1. Thus, the mole ratio of hydrogen to carbon monoxide initially fed may be 1:1 while during the hydroformylation reaction said ratio may be increased. The hydrogen to carbon monoxide mole ratios fed initially or later should not be less than 1:1, but it may be greater than 1:1. Generally, the mole ratio of hydrogen to carbon monoxide is kept between 1:1 to 5:1, preferably between 1:1 to 3:1.

Although normally, liquid organic solvents which are inert or which do not interfere to any substantial degree with the desired hydroformylation reaction may be used in the process of the invention, better results are obtained without a solvent.

The partial pressure of carbon monoxide may be lowered during the hydroformylation reaction by any of several methods which effectively reduce the carbon monoxide partial pressure. For example, the reduction of the total pressure of an equimolar mixture of carbon monoxide and hydrogen as the reaction proceeds. Alternatively, the total pressure may be kept constant, while the partial pressure of hydrogen is increased thereby decreasing the carbon monoxide partial pressure. Again, the total pressure may be kept constant, but the partial pressures of both the carbon monoxide and the hydrogen is decreased by the addition of an inert gaseous diluent, such as nitrogen.

The process can be carried out in a batch operation by simply reducing the carbon monoxide partial pressure by any of the above procedures at some regular intervals during the reaction. The process also can be carried out on a continuous basis wherein the process stream is passed successively through a series of staged reactors in which the carbon monoxide partial pressure is lowered in each successive stage. The continuous process is preferred. The process may also be carried out in a continuous flow reactor in which the olefinic reactant containing the complexed rhodium catalyst and gaseous reactants are concurrently introduced.

The partial pressure of hydrogen is not critical to the operation of the process. A very high partial pressure of hydrogen should be avoided particularly in the early stages of reaction, because the hydrogenation of olefin may occur as a competing reaction. In general, the initial hydrogen partial pressure may vary from 20 to 300 psia.

The rhodium catalyst concentration is not critical to the success of the process. In general, rhodium concentrations from $10^{-5}$ to $10^{-2}$ moles of rhodium per mole of olefin, i.e., compound may be used. A concentration from about $10^{-4}$ to about $5 \times 10^{-3}$ mole rhodium per mole of olefin is preferred. Methods for preparing the rhodium catalysts of the process of the invention are described in U.S. Pat. No. 3,527,809 which is hereby incorporated by reference. A suitable method is to heat a carbon monoxide complex of rhodium, such as hexarhodium hexadecacarbonyl, with the triorgano phosphorous ligand to replace one or more of the carbon monoxide molecules producing an active catalyst which is soluble in the olefinic reactant.

The process of the invention can be conducted at temperatures from as low as 60° C. up to 150° C. with good results. Temperatures in the range of 90° to 120° C. are preferred. Temperatures above 150° C. will give the higher linear to branched aldehyde ratios of this invention, but undesirably side reactions result in the loss of reactants to byproducts.

The process of the present invention results in the preparation of a reaction product made up of aldehydes with a high ratio of linear to branched chain aldehydes, catalyst complex, excess ligand and byproduct. Byproducts usually include hydrogenated products and polymeric products.

The aldehydes produced by the process of the present invention are separated from the reaction product by conventional means, e.g., distillation before they are used to prepare alcohols.

In the following examples, which further illustrate the process of the invention, all percentages are by weight unless otherwise stated and the pressures are all expressed as psig (pounds per square inch guage). Atmospheric pressure is equal to 0 psig.

EXAMPLE 1

(Partial Pressure of Carbon Monoxide Reduced by Reducing the Total Pressure)

A mixture of 0.25 mole of 2-vinyl-4-methyl-1,3-dioxane (4-VMD), $4.7 \times 10^{-5}$ moles hexarhodium hexadecacarbonyl (790 ppm Rh) and 0.015 mole of triphenyl phosphite was heated at 90° C. in a stirred glass pressure vessel. When a homogenous solution was obtained, an equimolar mixture of carbon monoxide and hydrogen was introduced at an initial pressure of 60 psig. The reaction temperature was maintained at 90° C. As the reaction proceeded, the total pressure of the above gaseous mixture was gradually reduced stepwise through a pressure regulator according to the schedule below. Samples of the reaction mixture were withdrawn at the times shown and the samples analyzed by a gas chromatographic technique for unreacted starting material and for the linear aldehyde and the branched aldehyde. A comparison of the time to reach a given conversion of 4-VMD in this example and Comparative Example 1 (hereinafter described) shows that the reaction rate in the process of the invention was 60 minutes for 96% conversion of 4-VMD as compared to 65 minutes for 92% conversion of 4-VMD.

| Time, Min. | % of 4-VMD Reacted | Total Pressure psig | % Conversion To Aldehydes | % Aldehydes As Linear Isomer | % Aldehydes As Branched Isomer |
|---|---|---|---|---|---|
| 2 | 17 | 60 | 12 | 85 | 15 |
| 4 | 26 | 60 | 21 | 87 | 13 |
| 8 | 42 | 40 | 36 | 89 | 11 |
| 25 | 70 | 20 | 64 | 91 | 9 |
| 40 | 86 | 10 | 80 | 92 | 8 |
| 60 | 96 | 10 | 90 | 92 | 8 |

EXAMPLE 2

(The Partial Pressure of Carbon Monoxide was Reduced by Reducing the Total Pressure)

The hydroformylation was carried out as described in Example 1 except that the starting pressure of the CO and $H_2$ mixture was 40 psig and the pressure was reduced according to that shown in the following schedule to yield the indicated linear and branched chain aldehydes.

| Time, Min. | % of 4-VMD Reacted | Total Pressure psig | % Conversion To Aldehydes | % Aldehydes As Linear Isomer | % Aldehydes As Branched Isomer |
|---|---|---|---|---|---|
| 4 | 17 | 40 | 13 | 94 | 6 |
| 8 | 30 | 40 | 24 | 94 | 6 |
| 15 | 42 | 40 | 36 | 95 | 5 |
| 25 | 57 | 20 | 50 | 95 | 5 |
| 40 | 76 | 20 | 69 | 95 | 5 |
| 60 | 90 | 20 | 84 | 95 | 5 |

EXAMPLE 3

(The Partial Pressure of Carbon Monoxide was Reduced by Reducing the Total Pressure)

The hydroformylation was carried out as described in Example 1 except that the reaction was run at 95° C. and the pressure was reduced according to that shown in the following schedule to yield the indicated linear and branched chain aldehydes.

| Time, Min. | % of 4-VMD Reacted | Total Pressure psig | % Conversion To Aldehydes | % Aldehydes As Linear Isomer | % Aldehydes As Branched Isomer |
|---|---|---|---|---|---|
| 4 | 20 | 60 | 15 | 90 | 10 |
| 15 | 53 | 40 | 47 | 92 | 8 |
| 25 | 67 | 20 | 61 | 93 | 7 |
| 40 | 83 | 10 | 77 | 93.5 | 6.5 |
| 60 | 96 | 10 | 90 | 94 | 6 |

EXAMPLE 4

(The Partial Pressure of the Carbon Monoxide was Reduced by the Addition of an Inert Gas)

A mixture of 0.25 mole 4-VMD, 790 ppm rhodium and 0.015 mole triphenyl phosphite was heated to 90° C. in the stirred glass pressure vessel of Example 1. The reaction was run at a constant pressure of 40 psig. The gas composition was changed during the progress of reaction by the addition of nitrogen according to the schedule indicated to yield the indicated linear and branched aldehydes.

| Time, Min. | % of 4-VMD Reacted | Gas Composition | $P_{CO}$ psig | Conversion to Aldehydes | % of Aldehyde As Linear Isomer |
|---|---|---|---|---|---|
| 4 | 14 | 50% CO, 50% $H_2$ | 20 | 11 | 91.5 |
| 10 | 33 | 50% CO, 50% $H_2$ | 20 | 28 | 92 |
| 15 | 49 | 45% CO, 45% $H_2$, 10% $N_2$ | 18 | 42 | 93 |
| 25 | 64 | 36% CO, 36% $H_2$, 28% $N_2$ | 14 | 56 | 93.5 |
| 40 | 78 | 12% CO, 12% $H_2$, 76% $N_2$ | 5 | 72 | 94 |

EXAMPLE 5

(The Partial Pressure of Carbon Monoxide was Reduced by the Addition of Hydrogen)

The hydroformylation was carried out as described in Example 1 except that the reaction mixture was heated to 90° C. and reacted at 40 psig constant pressure with a gas mixture whose composition was varied according to the schedule indicated to yield the indicated linear and branched aldehydes.

| Time, Min. | % of 4-VMD Reacted | Gas Composition | $P_{CO}$ psig | % of Aldehydes As Linear Isomer |
|---|---|---|---|---|
| 4 | 14 | 50% CO, 50% $H_2$ | 20 | 95 |
| 8 | 22 | 46% CO, 54% $H_2$ | 18.4 | 94 |
| 15 | 43 | 41% CO, 59% $H_2$ | 16.4 | 94 |
| 25 | 64 | 30% CO, 70% $H_2$ | 12 | 95 |
| 40 | 95 | 25% CO, 75% $H_2$ | 10 | 95.5 |

This reaction also produced 8% of the hydrogenation product, 2-ethyl-4-methyl-1,3-dioxane (hydrogenated olefin).

EXAMPLE 6

Example 5 was reported except that it was run at 100° C., and the gas composition was varied according to the following schedule to yield the indicated linear and branched aldehydes.

| Time, Min. | % of 4-VMD Reacted | Gas Composition | $P_{CO}$ psig | % of Aldehydes As Linear Isomer |
|---|---|---|---|---|
| 4 | 17 | 50% CO, 50% $H_2$ | 20 | 96 |
| 8 | 31 | 50% CO, 50% $H_2$ | 20 | 96 |
| 15 | 49 | 50% CO, 50% $H_2$ | 20 | 96 |
| 25 | 70 | 43% CO, 57% $H_2$ | 17 | 95 |
| 35 | 89 | 40% CO, 60% $H_2$ | 16 | 95 |
| 45 | 98 | 36% CO, 64% $H_2$ | 14.5 | 94.5 |

In this example only 2% of the hydrogenated product, 2-ethyl-4-methyl-1,3-dioxane was produced.

COMPARATIVE EXAMPLE 1

(The Partial Pressure of Carbon Monoxide is Held Constant)

A sample of 0.25 mole of 4-VMD was added to a catalyst solution prepared from 0.015 mole triphenyl phosphite, 790 ppm rhodium and 11 ml of 2-ethyl-4-methyl-1,3-dioxane in the stirred glass pressure vessel of Example 1. The reaction was carried out at 95° C. with a constant pressure of 40 psig of an equimolar mixture of CO and H$_2$. The partial pressure of carbon monoxide was maintained at 20 psig. The linear and branched aldehyde compositions during the progress of the hydroformylation are shown below. The linear aldehyde content decreased with increasing conversion.

| Time, Min. | % of 4-VMD Reacted | Conversion To Aldehydes | % of Aldehydes As Linear Isomer | % of Incremental Aldehyde as Linear |
|---|---|---|---|---|
| 6 | 18 | 17 | 87.5 | — |
| 10 | 28 | 27 | 88.8 | — |
| 15 | 42 | 42 | 87.2 | 84 |
| 25 | 58 | 56 | 84.2 | 76 |
| 40 | 76 | 75 | 81.7 | 74 |
| 65 | 92 | 91 | 78.5 | 63 |

COMPARATIVE EXAMPLE 2

(Effect of Lower Catalyst Concentration and Constant Carbon Monoxide Pressure on Linear and Branched Aldehydes)

A mixture of 0.25 mole 4-VMD, 180 ppm rhodium and 0.0007 mole triphenyl phosphite was reacted in the glass pressure vessel of Example 1 at 95° C. with a constant pressure of 40 psig of an equimolar mixture of carbon monoxide and hydrogen. The partial pressure of carbon monoxide was maintained at 20 psig. The linear and branced aldehyde produced is shown below. The linear isomer content decreased with increased conversion.

| Time, Min. | % of 4-VMD Reacted | Conversion To Aldehydes | % of Aldehydes As Linear Isomer | % of Incremental Aldehyde as Linear |
|---|---|---|---|---|
| 6 | 11 | 11 | 86 | — |
| 10 | 24 | 19 | 85.6 | 85 |
| 25 | 46 | 39 | 80.7 | 76 |
| 40 | 71 | 67 | 79.4 | 77 |

COMPARATIVE EXAMPLE 3

(Constant Carbon Monoxide Partial Pressure)

The comparative Example 2 was repeated in a 300 ml stainless steel autoclave stirred at 2,000 rpm with a turbine-type agitator with a hollow shaft. A mixture of 0.5 mole 4-VMD, 170 ppm rhodium and 0.003 mole triphenyl phosphite was reacted at 100° C. with a constant pressure of 60 psig of an equimolar mixture of carbon monoxide and hydrogen. The partial pressure of carbon monoxide was maintained at 30 psig. The linear and branched aldehyde formed is shown below. The linear isomer content decreased with increased conversion.

| Time, Min. | % of 4-VMD Reacted | Conversion To Aldehydes | % of Aldehydes As Linear Isomer | % of Incremental Aldehyde as Linear |
|---|---|---|---|---|
| 2 | 15 | 15 | 77.9 | — |
| 4 | 32 | 32 | 75.3 | 73 |
| 7 | 48 | 48 | 74.3 | 72.5 |
| 12 | 71 | 69 | 73.9 | 73.0 |
| 20 | 89 | 87 | 72.6 | 67.8 |

COMPARATIVE EXAMPLE 4

(Constant Carbon Monoxide Partial Pressure)

A sample of 100 ml of a 2 molar solution of 4-VMD in the solvent, 2-ethyl-4-methyl-1,3-dioxane, containing 58 ppm rhodium and 0.0038 mole phosphite was reacted at 90° C. with a constant pressure of 60 psig of an equimolar mixture of CO and H$_2$ in a 300 ml stainless steel autoclave. The partial pressure of carbon monoxide was maintained at 30 psig. The linear and branched aldehyde formed is shown below. The linear isomer content decreased with increased conversion.

Comparative Examples 1 to 4 clearly illustrate that the preparation of linear aldehyde decreases as the reaction proceeds. Various catalysts levels do not prevent the decrease in linear isomer. A comparison with the examples of the invention shows that the reaction rate in the process of the invention is generaly not less than in the process of the comparative examples.

| Time, Min. | % of 4-VMD Reacted | Conversion To Aldehydes | % of Aldehydes As Linear Isomer | % of Incremental Aldehyde as Linear |
|---|---|---|---|---|
| 1.5 | 16 | 17 | 61 | — |
| 3.0 | 30 | 31 | 59 | 56 |
| 6.0 | 52 | 51 | 57 | 54 |
| 10.0 | 71 | 70 | 56 | 53 |
| 17.0 | 89 | 86 | 55 | 51 |

The linear to branced chain aldehyde isomer ratio achieved by the process of this invention is greater than that achieved according to conventional procedures. In the process of this invention the linear to branched aldehyde molar ratios generally attained are at least 70/30. Ratios of 89/11 to 96/4 are generally attained when a cyclic acetal of acrolein is hydroformylated.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. In a process for the hydroformylation of a terminally unsaturated cyclic or acyclic olefinic compound having 3 to 20 carbon atoms in the presence of hydrogen and carbon monoxide at a molar ratio of 1:1 or greater of hydrogen to carbon monoxide and a rhodium complex catalyst to prepare a corresponding aldehyde, the improvement wherein the olefinic compound is a cyclic acetal of acrolein, the initial total pressure of carbon monoxide and hydrogen is from 40 to 500 psia, the initial partial pressure of the carbon monoxide is from 20 to 200 psia and the partial pressure of carbon monoxide is continuously or stepwise reduced at least 25% as the reaction proceeds from said initial range to a final range of 20 to 300 psia total pressure and 1 to 40 psia carbon monoxide partial pressure.

2. The improvement of claim 1 wherein the cyclic acetal of acrolein is 2-vinyl-5-methyl-1,3-dioxane.

3. An improvement for the preparation of aldehydes having a high ratio of linear to branched chains which comprises (a) initiating the hydroformylation of a cyclic acetal of acrolein in the presence of a rhodium complex catalyst at an initial total pressure of from 40 to 500 psia of hydrogen and carbon monoxide and an initial carbon monoxide partial pressure of from 20 to 200 psia, with carbon monoxide and hydrogen gas having initially a molar ratio of hydrogen to carbon monoxide of at least 1:1 at a temperature of from 60° to 150° C.;

(b) reducing continuously or stepwise the partial pressure of carbon monoxide at least 25%, as the reaction in (a) proceeds, until the carbon monoxide partial pressure is from 1 to 40 psia and the total pressure is from 20 to 300 psia to form a corresponding aldehyde with a high ratio of linear to branched aldehydes in the reaction product; and (c) separating said aldehydes from the reaction product.

4. The improvement of claim 3 wherein the cyclic acetal of acrolein is 2-vinyl-5-methyl-1,3-dioxane.

5. The improvements of claim 3 wherein the mole ratio of hydrogen to carbon monoxide is from 1:1 to 5:1.

6. The improvement of claim 3 wherein the mole ratio of hydrogen to carbon monoxide is from 1:1 to 3:1.

7. The improvement of claim 3 wherein the temperature is from 90° to 120° C.

8. The improvement of claim 3 wherein the carbon monoxide partial pressure is reduced at least 50%.

9. The improvement of claim 3 wherein the carbon monoxide partial pressure is reduced from 50 to 75%.

10. The improvement of claim 4 wherein the carbon monoxide partial pressure is reduced at least 50%.

11. The improvement of claim 4 wherein the carbon monoxide partial pressure is reduced from 50 to 75%.

* * * * *